United States Patent
Guala

(10) Patent No.: US 6,537,258 B1
(45) Date of Patent: Mar. 25, 2003

(54) VALVE FOR MEDICAL INFUSION LINES AND THE LIKE

(75) Inventor: Gianni Guala, Turin (IT)

(73) Assignee: Industrie Borla SpA (IT)

( * ) Notice: Subject to any disclaimer, the term of this patent is extended or adjusted under 35 U.S.C. 154(b) by 0 days.

(21) Appl. No.: 09/706,119

(22) Filed: Nov. 3, 2000

(30) Foreign Application Priority Data

| Dec. 14, 1999 | (IT) | ......................................... | TO99A1093 |
| Nov. 12, 1999 | (IT) | ......................................... | TO99A 0975 |
| Jun. 13, 2000 | (IT) | ......................................... | TO00A0571 |

(51) Int. Cl.⁷ .............................................. A61M 5/00
(52) U.S. Cl. ........................ 604/247; 604/256; 137/522; 251/149.1
(58) Field of Search .............................. 604/9, 10, 249, 604/132, 246, 247, 256, 905; 251/149.1; 137/843, 522

(56) References Cited

U.S. PATENT DOCUMENTS 5,465,938 A * 11/1995 Werge et al. ............ 251/149.1
5,509,436 A * 4/1996 Japuntich et al. ............. 137/15

\* cited by examiner

Primary Examiner—Anhtuan T. Nguyen
Assistant Examiner—Matthew DeSanto
(74) Attorney, Agent, or Firm—TraskBritt

(57) ABSTRACT

A check valve and, in particular, an anti-siphon valve, for medical infusion lines and the like, including an axial upstream passageway and an axial downstream passageway, staggered and parallel with respect to each other, and a diaphragm of elastic material cooperating with an annular valve seat for normally keeping communication between these passageways closed. The diaphragm is composed of the end wall of a cup-shaped element on which a plunger rests coaxially, the plunger being slidable between a retracted inoperative position and an advanced operative position. Valve opening occurs following flexion of the diaphragm, which can be spontaneous due to a predetermined fluid pressure developing in the upstream passageway, or positively operated via the plunger (9).

34 Claims, 13 Drawing Sheets

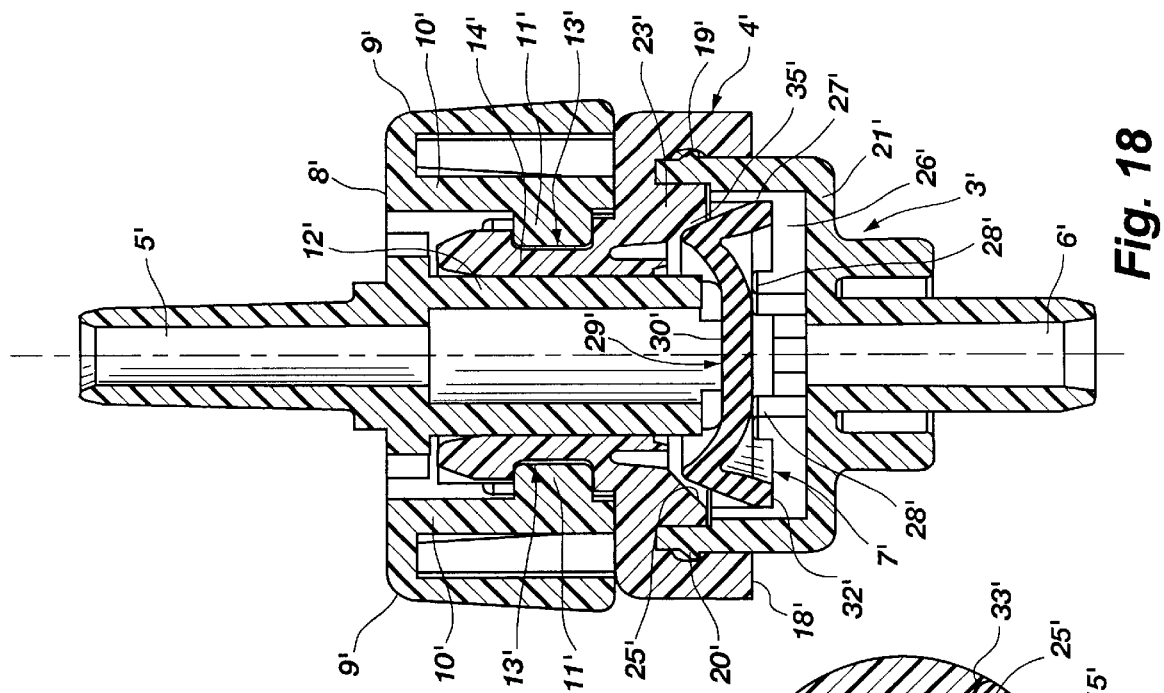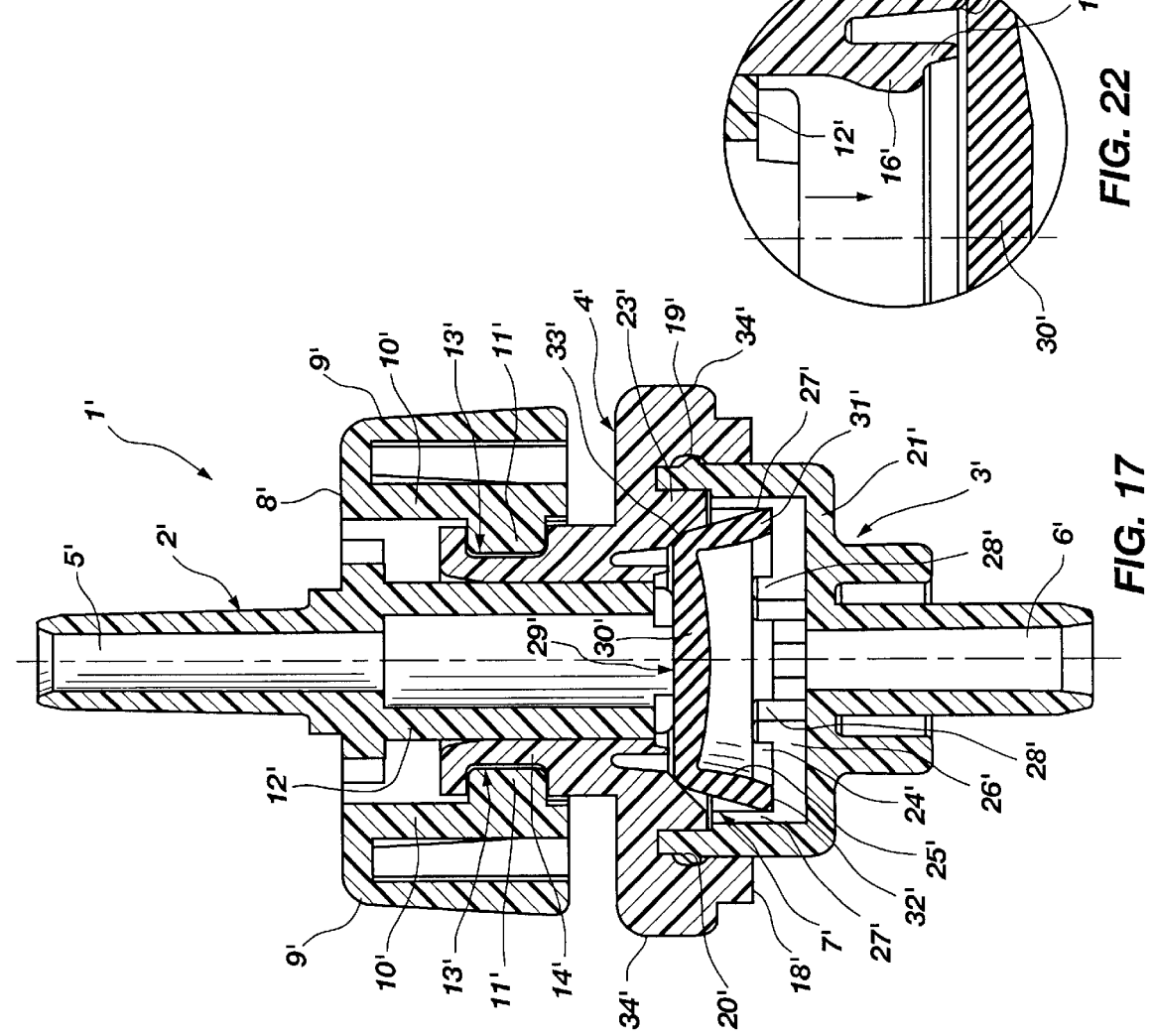

VALVE FOR MEDICAL INFUSION LINES AND THE LIKE

BACKGROUND OF THE INVENTION

The present invention refers to check valves for medical infusion lines and the like. More in particular, the invention regards an anti-siphon (or non-return) valve for such medical lines.

These valves traditionally include a first and a second tubular element mutually coaxial to each other and respectively defining an upstream passageway and a downstream passageway, a diaphragm of elastically deformable material transversely positioned between said first and a second tubular elements and acting as a fluid seal in combination with an annular valve seat to keep the said control valve normally closed, wherein a predetermined fluid pressure in the said upstream passageway causes flexion of the said diaphragm and the consequent opening of the valve.

These valves, which are normally closed, must be capable of promptly opening when the pressure in the upstream passageway exceeds a predetermined threshold. In the particular case of an anti-siphon valve, this threshold is much higher than in the normal check valves used in similar medical applications, and is typically in the range from 1 to 5 psi.

In addition, in some applications and particularly in the case of anti-siphon valves, it must be possible to control the opening of the valve diaphragm independently of the pressure in the upstream passageway. This manoeuvre can be required, for example, in cases of priming a pump (normally a peristaltic pump) associated with the medical line, when the infusion must be given under the effect of gravity, or also when the medical line is washed or bled.

SUMMARY OF THE INVENTION

The object of the present invention is to provide a check valve of the above-defined type, designed to meet the aforesaid requirement and with simple and low-cost manufacture, also with regards to assembling.

Another object of the invention is to provide a check valve of the above-defined type, the opening of which can be controlled in an easy and practical manner.

According to the invention, these objects are essentially achieved via the characteristics defined in claim 1.

Additional, advantageous, secondary characteristics of the valve are defined in sub- claims 2–42.

BRIEF DESCRIPTION OF THE DRAWINGS

The invention will now be described in detail with reference to the enclosed drawings, which are supplied purely as a non-limitative example, and where:

FIG. 17 is an axial section view along the XVII—XVII line of FIG. 15.

FIG. 18 is an axial section view along the XVIII—XVIII line of FIG. 16.

FIG. 22 shows a detail of FIG. 17 in greater scale, prior to assembling of the valve.

DETAILED DESCRIPTION OF THE INVENTION

Figure 1:
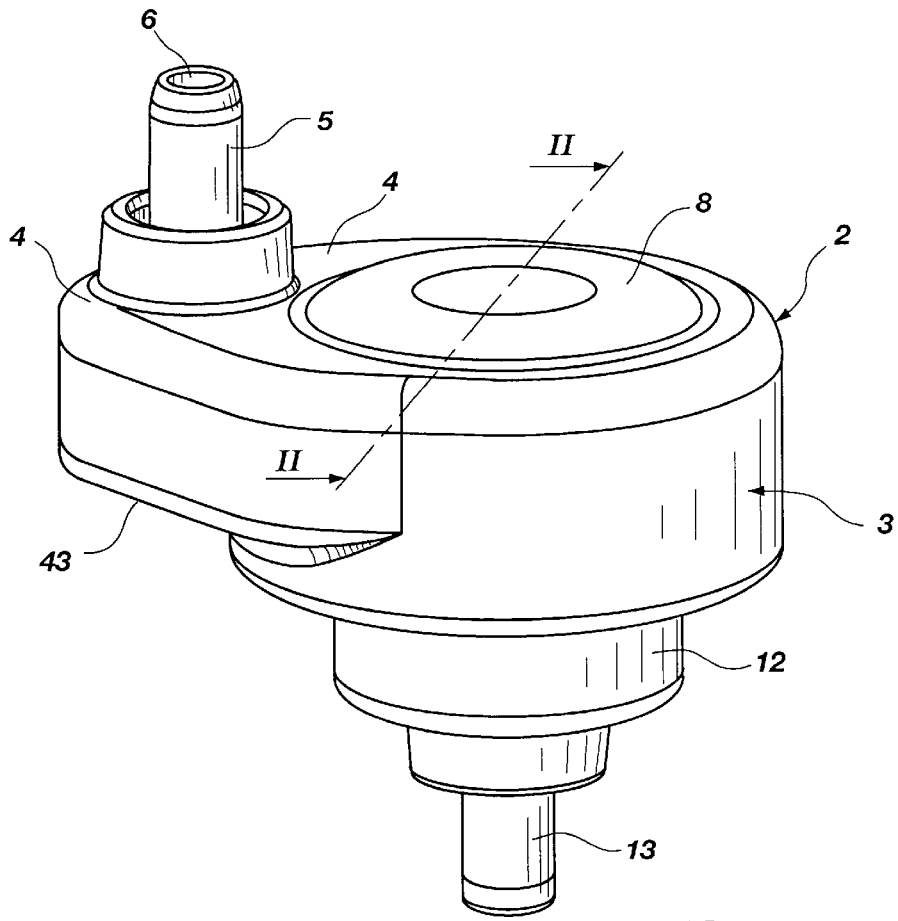
FIG. 1 is a schematic perspective view of a check valve in conformity with the invention.
Figure 2:
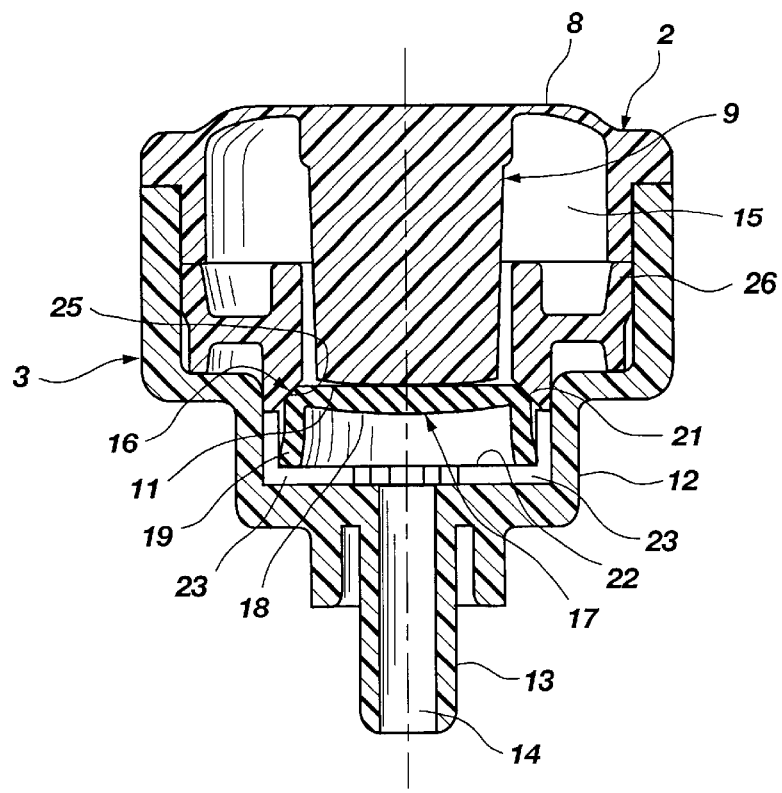
FIG. 2 is an axial section view along the II—II line of FIG. 1.
Figure 3:
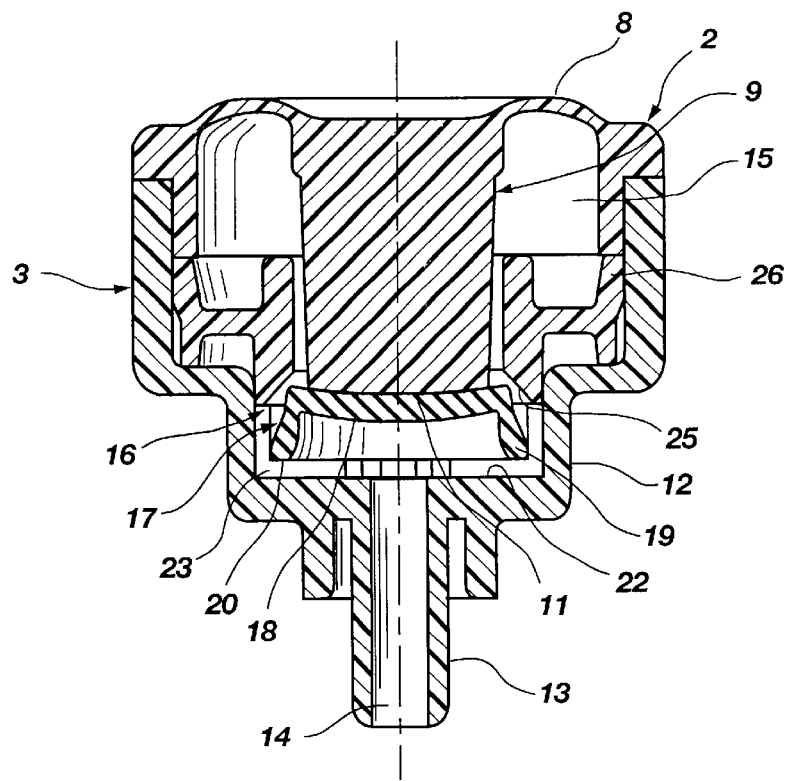
FIG. 3 is a similar view to that of FIG. 2, showing the valve in the controlled open position.

With initial reference to FIGS. 1–3, reference numeral 1 indicates a valve assembly in conformity with the invention, the illustration referring specifically to an anti-siphon valve for medical infusion lines and similar applications. In the case of the illustrated example, the valve (1) is designed for tube-to-tube connection: it should be noted however that it could also be set up for Luer-tube, tube-Luer or Luer-Luer connections.

The body of the valve (1) is composed of a two hollow parts, respectively indicated as 2 and 3, both of which are normally made of a suitable moulded thermoplastic material, such as polycarbonate, and permanently joined together using, for example, ultrasonic welding, gluing or equivalent systems. These parts are conveniently devoid of complex forms and can therefore be produced using relatively uncomplicated moulds.

The first part (2) is composed of an essentially circular-shaped cap with a lateral appendage (4) forming the first tubular element (5) that defines an upstream passageway, or inlet passageway (6).

Part 2 is moulded with an elastically sprung, annular wall of reduced thickness (8), which in turn is integrally moulded with a central cylindrical member (9) to form a control plunger, as will be explained in the following. In the illustrated example, the annular wall (8) has annular ribbings or corrugations arranged on axially staggered planes, thereby assuming the general shape of a spring.

The plunger (9) has a reduced-diameter spigot (10) at one end, forming a manual control member of the valve (1), while the other end (11) has a convex surface, for example spherical or simply flat.

As it will appear evident in the following, the elastically spring annular wall (8) forms an elastic member that tends to hold the plunger (9) in the retracted, inoperative position shown in FIG. 2. The elastic wall (8) is elastically deformable to allow the plunger (9) to move to the advanced, operative position shown in FIG. 3.

The second part (3) of the body of the valve (1) has a generally complementary form to that of the first part (2), one portion with a generally circular section (12) and a lateral appendage (43) corresponding to the lateral appendage (.4) of part 2. The circular portion (12) is integrally moulded with a second tubular connector (13) that defines a downstream passageway, or outlet passageway (14).

Parts 2 and 3 of the body of the valve (1) form between them a chamber (15) that communicates laterally with the first tubular connector (5), or rather with the inlet passageway (6), and is axially connected with the outlet passageway (14) via a one-way valve with both spontaneous and controlled opening, generally indicated as 16.

The valve (16) basically consists of an elastic obturator formed by a cup-shaped element (17), which has a circular end wall (18) and a shell or side wall (19) with a cylindrical shape or, more suitably, a diverging conical surface at the part opposite to the end wall (18).

The end wall (18) can be of even thickness or, more suitably, be thicker towards its centre. Similarly, the side wall (19) can be of even thickness or, more suitably, be thicker towards its free edge (20).

The external circumferential edge (21) of the end wall (18) can be sharp, as in the case of the illustrated example, or rounded.

The cup-shaped element (17) is normally moulded as a single piece of soft elastomeric material, especially liquid silicone that is injection moulded using a central injection point.

The cup-shaped element (17) is inserted, coaxially with the outlet passageway (14), so that it rests on the annular wall (22) of the second part (3) of the body of the valve (1), which has a channelled surface formed by a halo of radial channels (23) communicating with the outlet passageway (14). The radially external tip of each radial channel (23) is extended by a respective axial channel (24) moulded into wall of the second part (3) of the body of the valve (1) facing the side wall (19) of the cup-shaped element (17). The channelled surface (22) can also be formed around the outlet passageway (14) with axial ridges not shown in the drawings.

The external circumferential edge (21) of the end wall (18) of the cup-shaped element (17) rests against an annular valve seat (25) formed by the conical surface of a ring insert (26), housed and axially blocked inside the chamber (15), and coaxial with the outlet passageway (14). The axial plunger (9) slidably passes coaxially through the ring (26) with some radial play, the convex end (11) of the plunger resting against the external face of the end wall (18) of the cup-shaped element (17).

The annular valve seat (25), normally closed and sealed by the circumferential edge (21) of the cup-shaped element (17), communicates with the inlet passageway (6) via the chamber (15) and axial passages defined between the plunger (9) and the ring (26): in the case of the illustrated example, the plunger (9) is fashioned with longitudinal recesses and more suitably, as can be clearly seen in FIGS. 2 and 3, has a cross-shaped cross-section. This arrangement is nevertheless provided purely as an example.

The spigot (10) of the plunger (9) constitutes the manually operable control member for selectively controlling the opening of the valve, by correspondingly deforming the annular elastic wall (8).

Operation of the valve (16) is as follows.

The above described arrangement is such that in the assembled state of parts 2 and 3 of the body of the valve (1), the cup-shaped element (17) is subjected to a predetermined axial elastic preloading: thus the peripheral edge (21) of its end wall (18) is kept elastically pressed against the annular valve seat (25) by the axial force exerted by the side wall (19), as well as by the consequent radial force applied by the end wall (18) due to the conical shape of the valve seat (25). This condition corresponds to the normally closed position of the valve in conformity with the invention, whereby flow from the upstream passageway (6) to the downstream passageway (14) is prevented in an effective and safe manner.

When an overpressure exceeding a predetermined threshold (e.g. in the range 1–5 psi in the case of anti-siphon applications) develops in the upstream passageway (6), the valve passes immediately from the closed position to the open position due to flexion of the end wall (18) of the cup-shaped element (17), possibly combined with a partial axial elastic yielding of the side wall (19). This flexion, corresponding to that shown in FIG. 3, which illustrates the controlled and non spontaneous opening of the valve, causes the peripheral edge (21) to move away from the annular valve seat (25), producing an annular opening between them. The upstream passageway (6) is thus put in connection with the downstream passageway (14) via the chamber (15), the axial passages between the plunger (9) and the ring (26), the annular opening (44), the axial channels (24) and the radial channels (23).

As already stated, the spontaneous opening of the valve also occurs promptly even if the diaphragm formed by end wall (18) of the cup-shaped element (17) is subjected to high axial preloading for ensuring maximum safety and reliability in closure. In fact, the force imparted against the end wall (18) by the pressure reaching the threshold value causes its elastic deformation into an essentially concave hemispheric shape (as shown in FIG. 3), resulting in the peripheral edge (21) separating from the conical-surface valve seat (25) with a certain amount of amplification. Therefore, in practice a modest pressure beyond the threshold level is sufficient to cause the spontaneous opening of the valve in a rapid and immediate manner, reducing any risks of undesired adherence between the edge (21) and the valve seat (25), even after prolonged periods of valve closure that might prejudice opening.

Spontaneous return to the closed position of the valve (16) when the pressure balance between the upstream passageway (6) and the downstream passageway (14) is re-established, or in the case of overpressure in the downstream passageway (14), occurs immediately due to the end wall (18) of the cup-shaped element (17) returning to the non-deflected configuration with the relative peripheral edge (21) resting against the annular valve seat (25) (as shown in FIG. 2).

To control opening of the valve (16) it is sufficient to axially press on the spigot (10). Due to this force and the consequent advancement of the plunger (9) to the operative position against the elastic return imparted by the annular wall (8), the end wall (18) of the cup-shaped element (17) deforms in a completely similar manner to that previously described in reference to spontaneous opening.

The open state is then maintained until the spigot (10) is released. In this case, the plunger (9) is immediately returned to the retracted, inoperative position due to the return effect of the elastic wall (8) to the non-deformed starting position and the end wall (18) of the cup-shaped element (17) returns with its edge (21) in contact with the valve seat (25) to form a hermetic seal.

Figure 4:
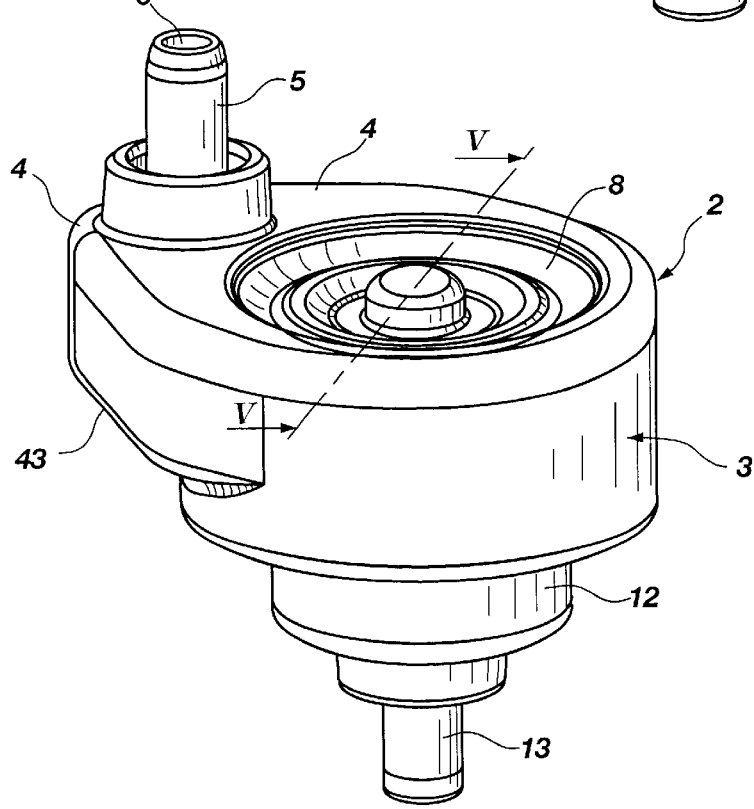
FIG. 4 is a schematic perspective view of a first variant of the check valve in conformity with the invention.
Figure 5:
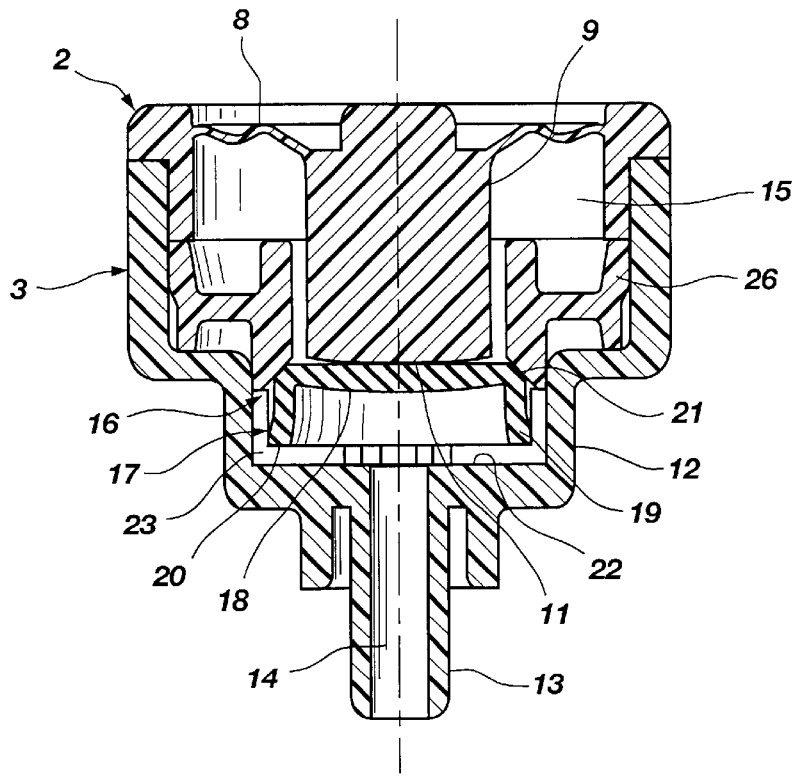
FIG. 5 is an axial section view along the VI—VI line of FIG. 4.
Figure 6:
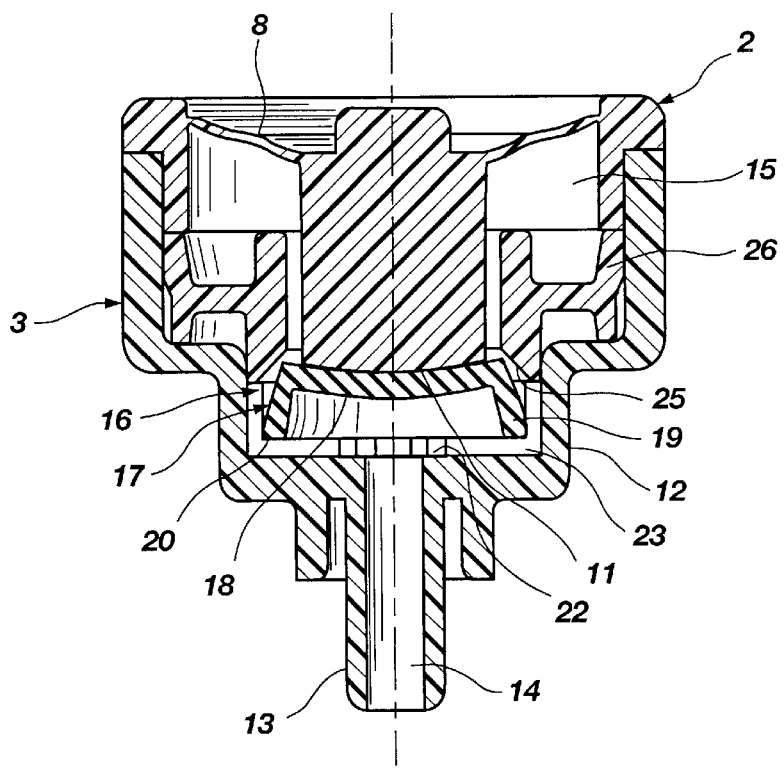
FIG. 6 is a similar view to that of FIG. 5, showing the valve in the controlled open position.
Figure 7:
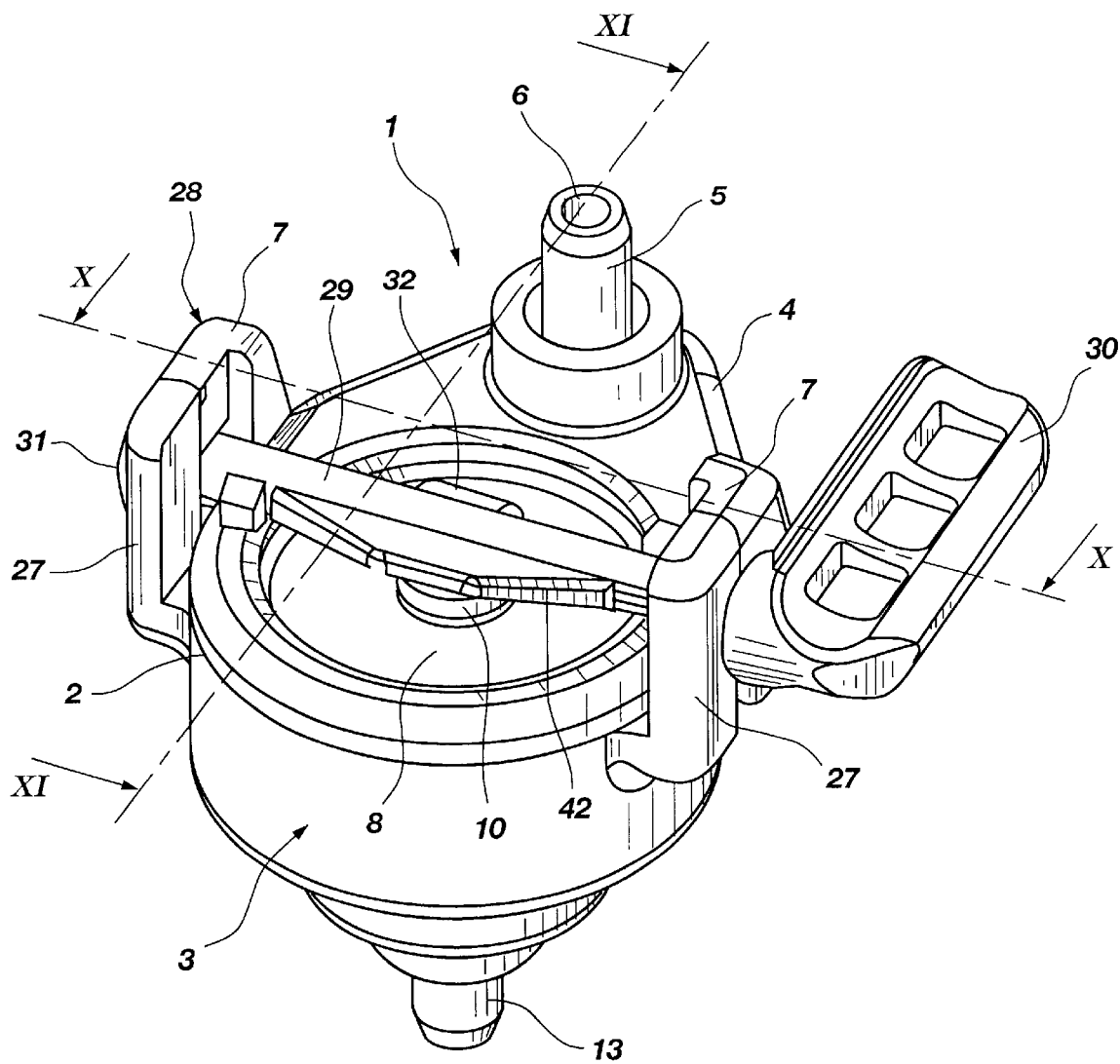
FIG. 7 is a schematic perspective view of a second variant of the check valve in conformity with the invention.

The embodiment illustrated in FIGS. 4–6 differs from that described above only in that the annular wall (8) has a rounded, substantially bell-shaped, external shape.

Naturally, the constructional details and the embodiments could be extensively changed with respect to that described and illustrated without leaving the scope of this invention. Thus, for example, a supplementary spring could be provided in addition to or in substitution of the annular wall (8).

In addition, although the valve has been described with express reference to an anti-siphon application, it could be also be easily adapted for use as a simple check valve with an opening control and preset for spontaneous opening at significantly smaller fluid pressure levels, e.g. 0.01–0.02 bar. Calibration can be effected by simply working on the elastic characteristics of the cup-shaped element (17), e.g. varying the thickness of its end wall (18), using materials of different hardness, or modifying the assembly preloading.

Finally, with regards to controlled opening, although the example illustrated in the drawings employs an axial push-down system, the external, manually induced deformation of the end wall (18) of the cup-shaped element (17) could also be effected using any type of equivalent system, e.g. such as a rotary system, even with motorised actuation.

The variant of the invention represented in FIGS. 7–12 is generally similar to that previously described and only the differences will be described in detail, using the same numerical references for similar or identical parts.

In this variant, the first part (2) is externally formed with a pair of diametrically opposed, axial struts (7). Between the external struts (7), part 2 has an elastically sprung annular wall (8) of reduced thickness, which in turn is integrally moulded with a central cylindrical member (9) to form a control plunger.

Figure 8:
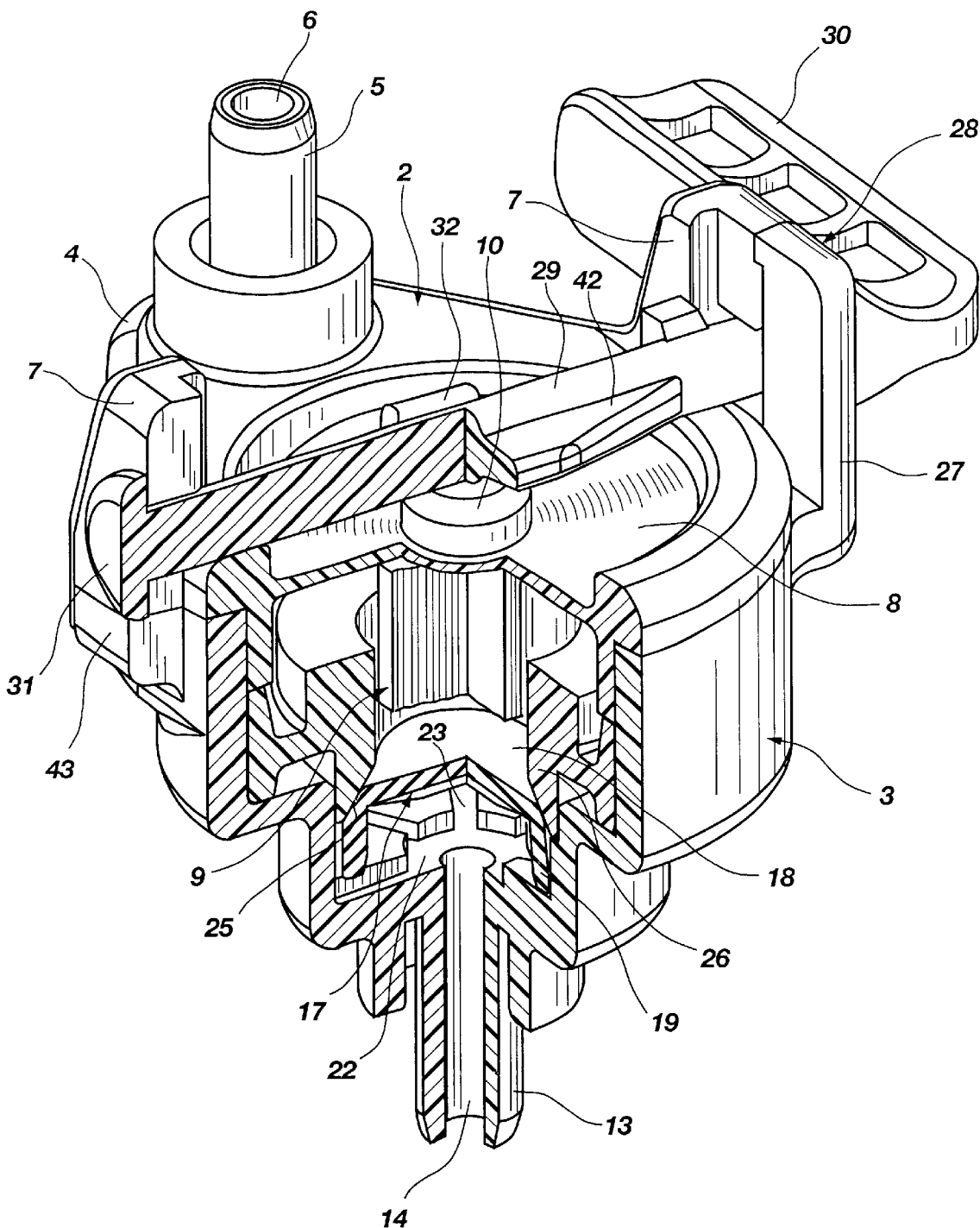
FIG. 8 is a similar view to that of FIG. 7, in larger scale and partially sectioned.
Figure 9:
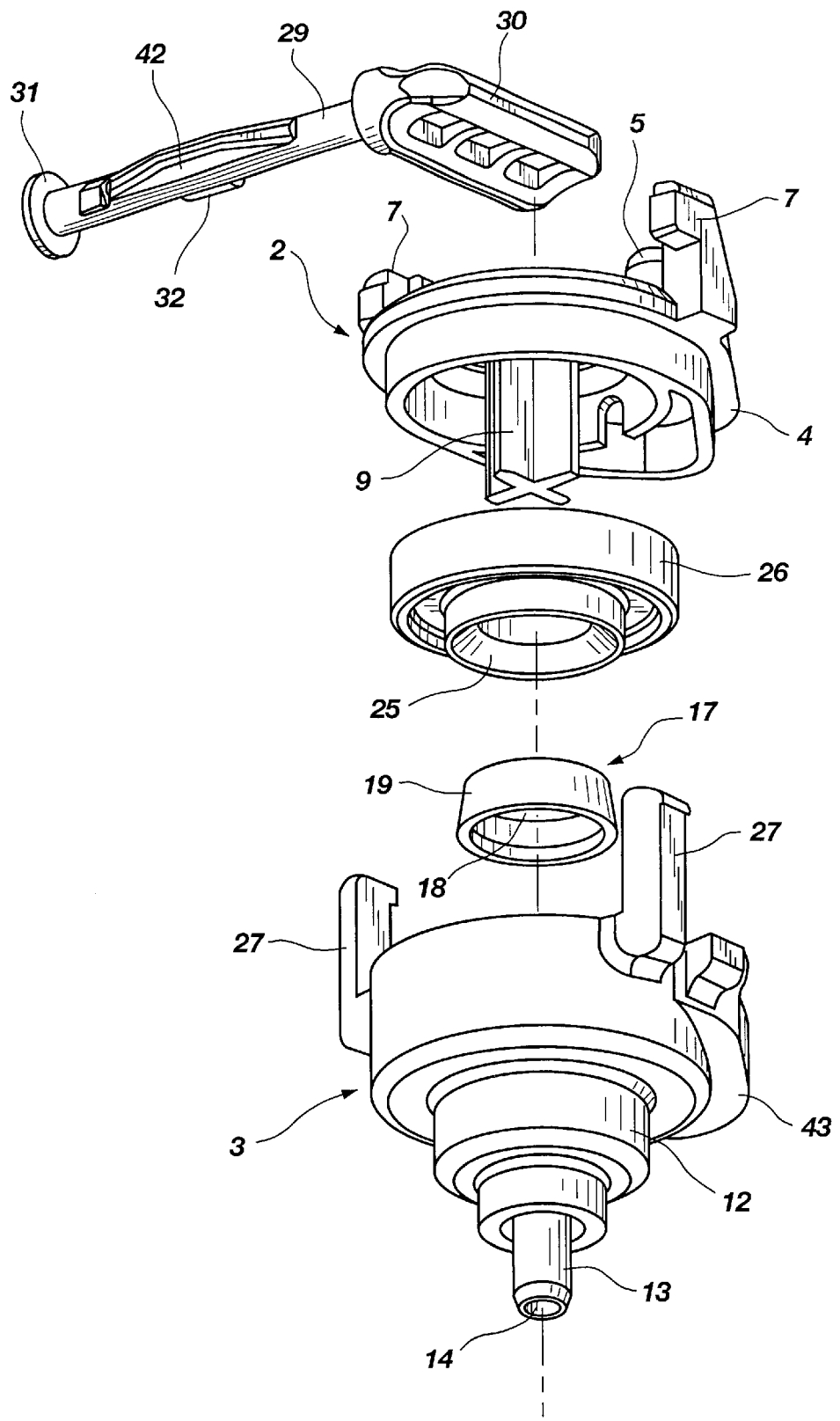
FIG. 9 is an exploded view of FIG. 7.
Figure 10:
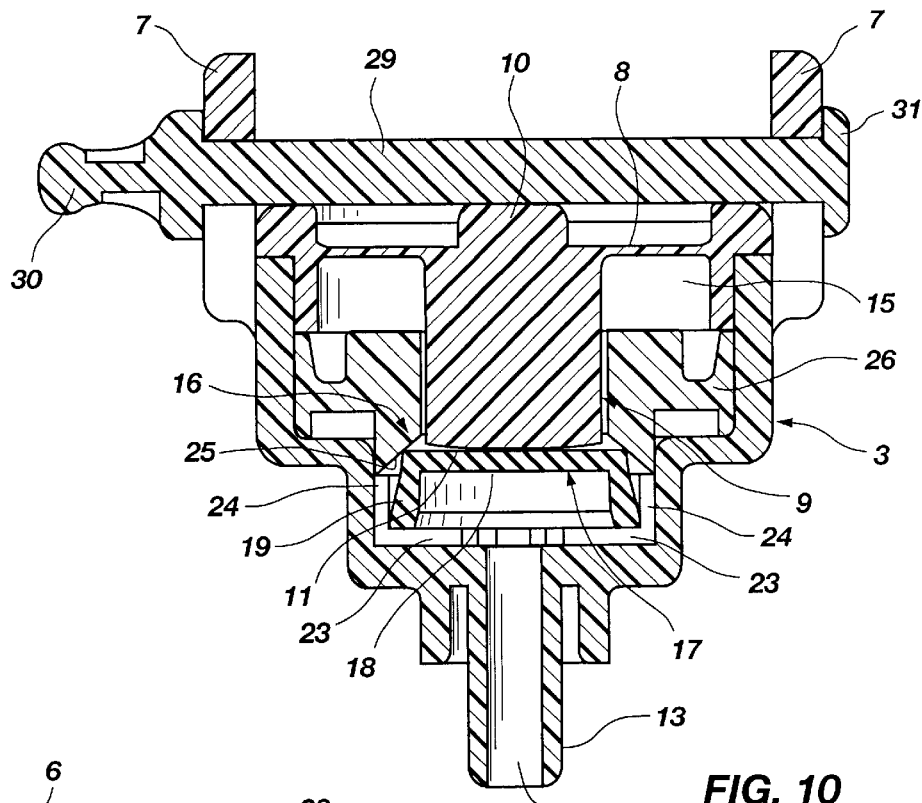
FIG. 10 is an axial section view along the X—X line of FIG. 7.
Figure 11:
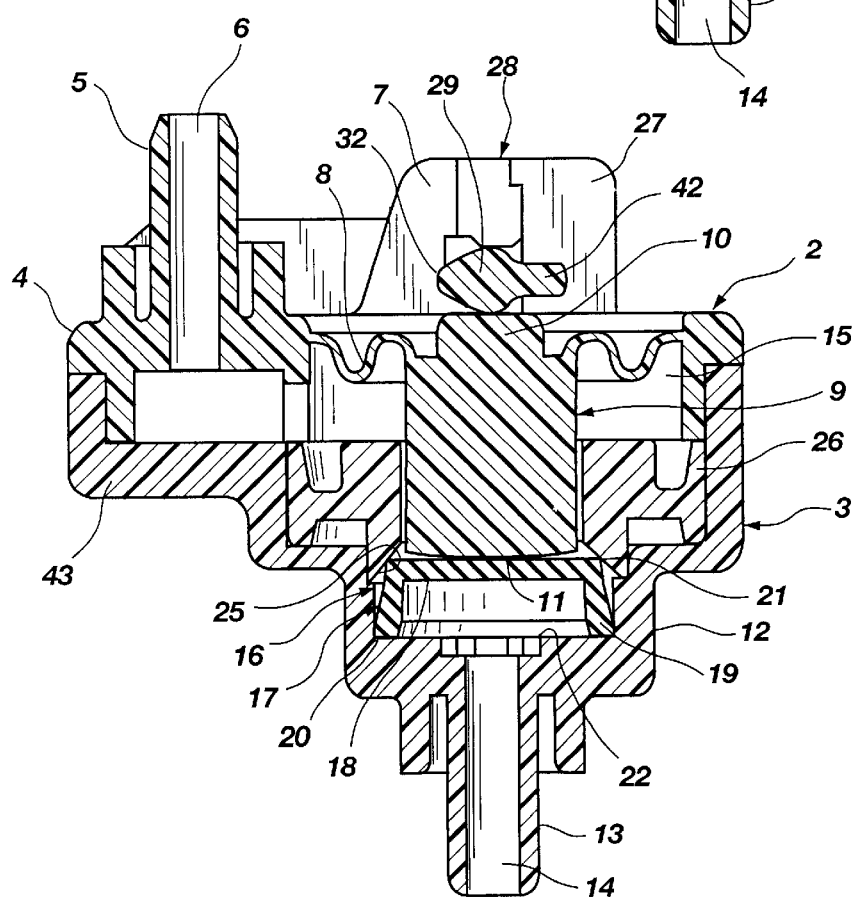
FIG. 11 is an axial section view along the XI—XI line of FIG. 7, in which another variant has been inserted.

Also in this case, the elastically sprung annular wall (8) constitutes an elastic member that tends to keep the plunger (9) in the retracted, inoperative position shown in FIGS. 8, 10 and 11. The elastic wall (8) is elastically deformable to allow the plunger (9) to extend to the advanced, operative position shown in FIG. 12 when in controlled operation mode.

It should be noted that the elastic annular wall (8) could have a different shape than that shown in FIG. 4, e.g. with annular ribbing as represented in the variant shown in FIG. 11.

Externally, the second part (3) of the body of the valve (1) has a pair of projecting axial struts (27), arranged to be diametrical opposite the axial struts (7) of part 2, and forming with these a fork support (28). A transverse rotating shaft (29), also normally made of a moulded plastic material and carrying a control appendage (30) at one end and an axial retaining disc (31) at the other, is mounted on the fork support (28). The transverse shaft (29) is arranged with the central zone in contact with the spigot (10) of the plunger (9) and has a radial projection (32) in correspondence with this zone, forming a cam. On the opposite side, the shaft (29) has a longitudinal reinforcement rib (42).

Figure 12:
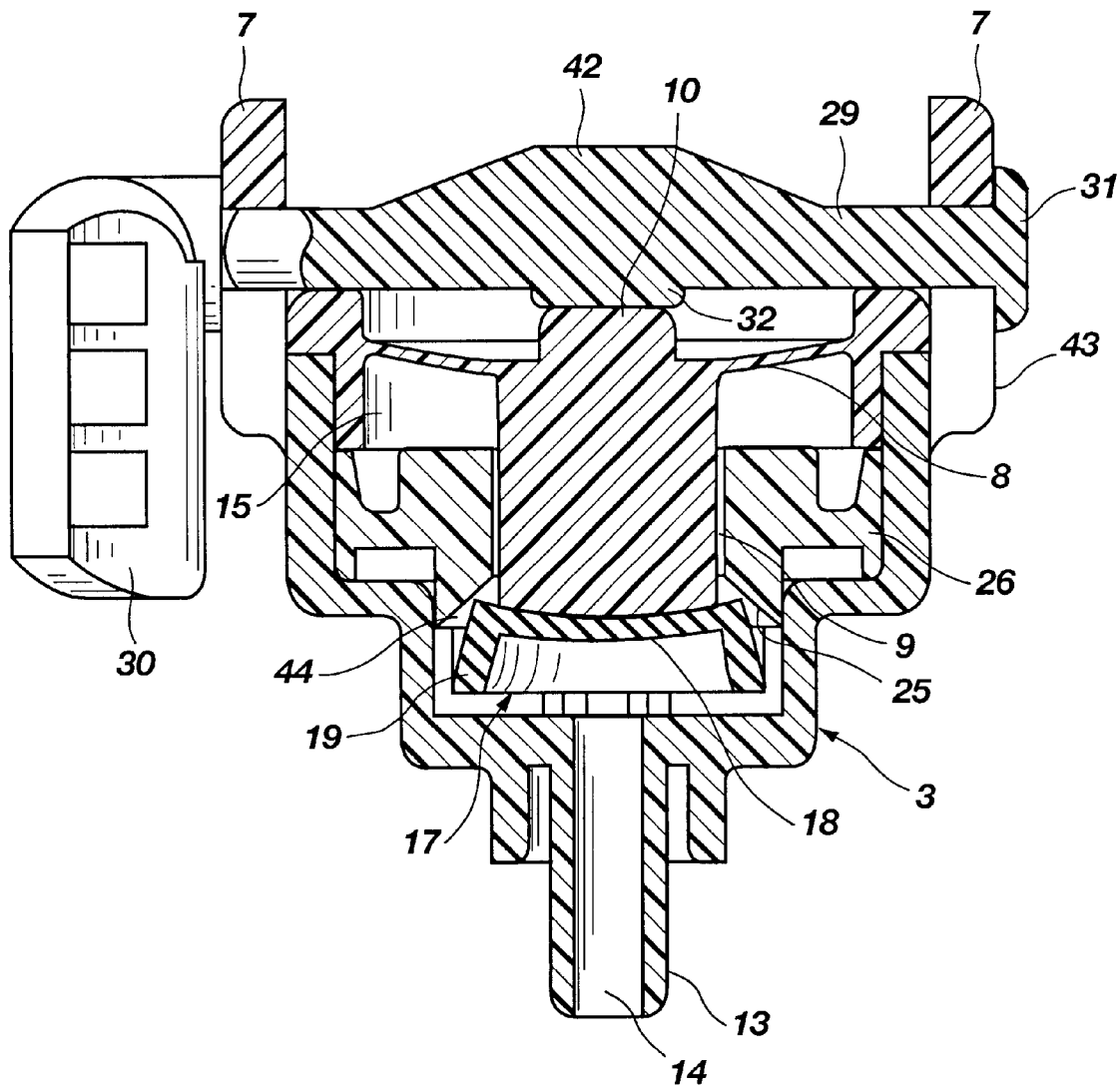
FIG. 12 is a similar view to that of FIG. 10, showing the valve in the controlled open position.

By operating the control member (30), the shaft (29) can be turned from the position shown in FIGS. 7–11, in which the cam (32) is staggered 90° with respect to the spigot (10) of the plunger (9), which is in the retracted, inoperative position, to the position shown in FIG. 12, in which the cam (32) holds the plunger (9) in the advanced operative position, with corresponding deformation of the elastic annular wall (8).

In operation, to open the valve it is sufficient to rotate the shaft (29) via the manual control (30) to the position shown in FIG. 12. Due to this rotation and the consequent advancement of the plunger (9) to the operative position via the cam (32) contrasting the elastic return action of the annular wall (8), the end wall (18) of the cup-shaped element (17) deforms in a totally similar manner to that previously described in reference to spontaneous opening The open state is thus maintained until the shaft (29) is turned back to the start position, as shown in FIGS. 8, 10 and 11. In this case, the plunger (9) is returned to the retracted, inoperative position due to the return effect of the elastic wall (8) to the non-deformed starting position and the end wall (18) of the cup-shaped element (17) returns with its edge (21) in contact with the valve seat (25) to form a hermetic seal.

In this case as well, many functionally equivalent variants can be envisaged: for example, with regards to controlled opening, even though the example illustrated in the drawings uses a rotating cam system, the external, manually induced deformation of the end wall (18) of the cup-shaped element (17) could also be effected using any other type of equivalent system, such as a sliding cam, inclined planes, or even a motorised actuator.

The variant illustrated in FIGS. 13 to 22 will now be described.

In this variant, item 1' indicates an axial fitting assembly for tube-to-tube connection in medical infusion lines and similar. It should be immediately noted that it could also be set up for Luer-tube, tube-Luer or Luer-Luer connections.

The fitting (1') is essentially composed of three components: a first tubular connector (2'), a second tubular connector (3') and an intermediate tubular element (4') that is rigidly fixed to the second tubular element (3') and on which the first tubular element (2') is mounted such that it can rotate.

The first tubular connector (2'), and the second tubular connector (3') are both normally constructed as single mouldings using a relatively rigid plastic material, such as polycarbonate or ABS, while the intermediate tubular element (4') is made as a single piece of a relatively less rigid plastic material, such as polyethylene, polypropylene, nylon or "vestodur". As it will appear evident in the following, the three components 2', 3' and 4' of the valve (1') are joined together using simple, irreversible snap couplings, without the need for additional mechanical connections. This evidently renders assembling of the valve (1') appreciably straightforward and economical.

Figure 19:
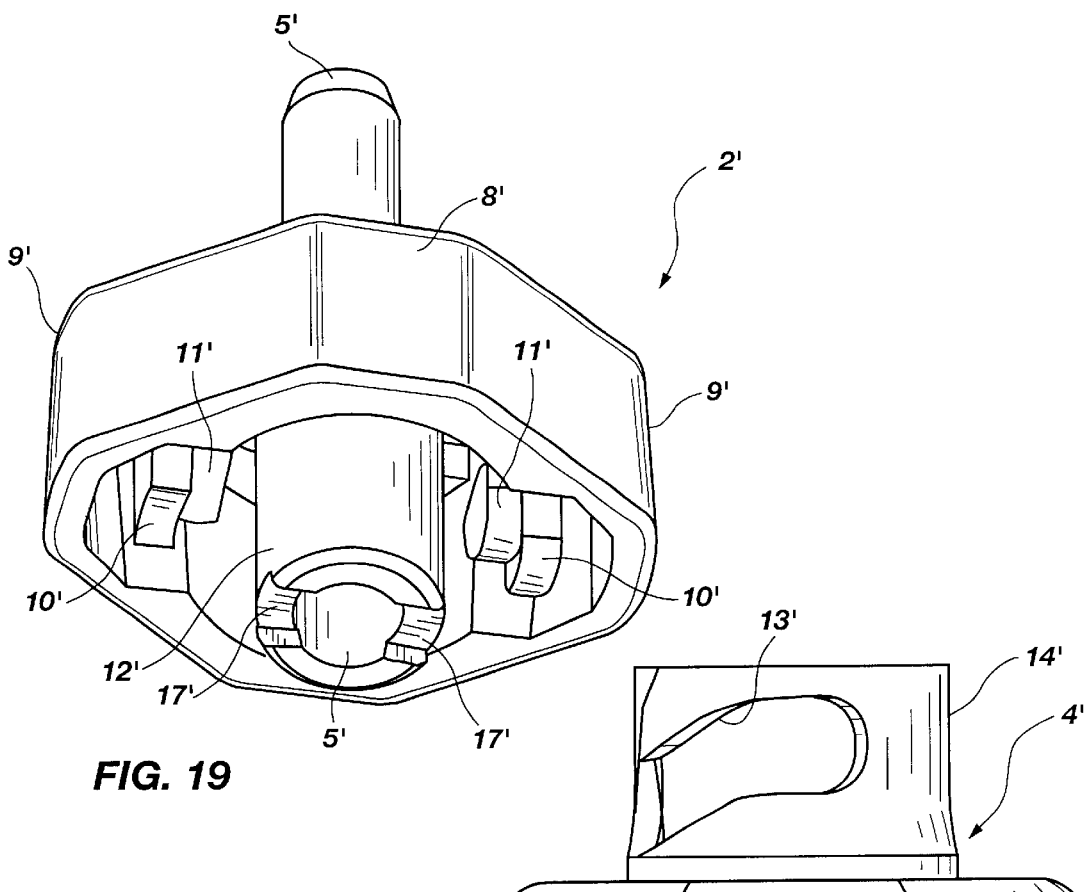
FIG. 19 is a perspective of a component of the valve viewed from below.
Figure 20:
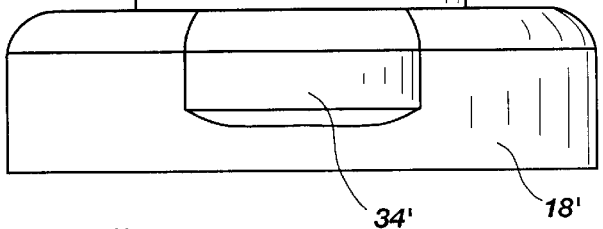
FIG. 20 is a side view of another component of the valve.
Figure 21:
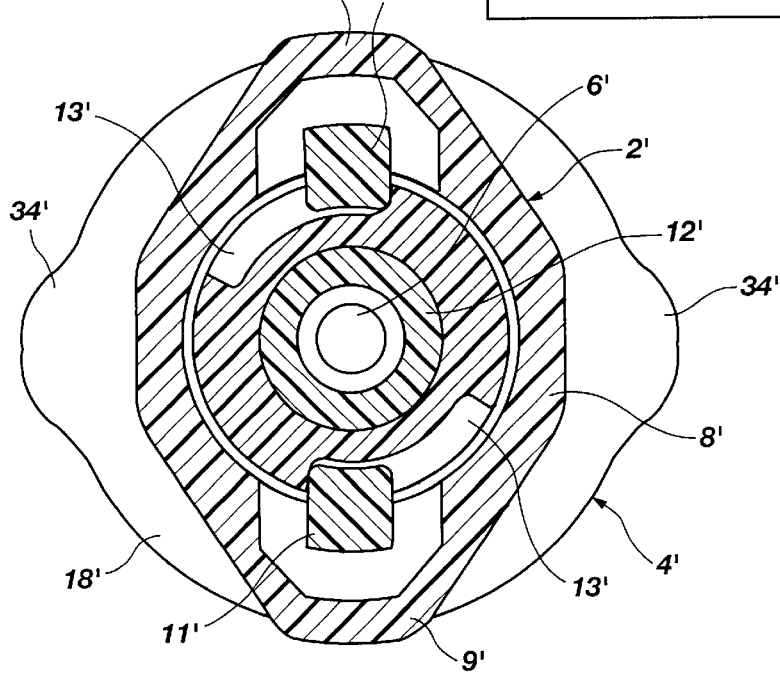
FIG. 21 is a larger-scale, cross section view along the XXI—XXI line of FIG. 16.

The first tubular connector (2'), illustrated in greater detail in FIG. 19, defines an upstream passageway, or inlet passageway (5'), coaxially aligned with a downstream passageway, or outlet passageway (6'), in the form of the second tubular connector (3'): these passageways can be connected to the respective tubing sections of a medical infusion line and the like.

An anti-siphon valve, generically indicated as item 7' and described in greater detail in the following, is inserted between the upstream passageway (5') and the downstream passageway (6').

The first tubular connector (2'), illustrated in greater detail in FIG. 19, includes a peripheral, axial shell (8') formed with two diametrically opposed, radially elongated portions (9')

respectively defining grip protuberances to facilitate valve opening and closing manoeuvres. Inside the peripheral shell (8'), the first tubular connector (2') has two axial appendages, in angular correspondence to the two grippers (9'), that are elastically sprung in the radial direction and, in turn, are equipped with ridges (11') radially projecting towards the inside and forming two cam-follower members, as will be seen in the following.

The portion of the upstream passageway (5') that faces the valve (7'), or rather the second tubular connector (3'), consists of a central, axial, tubular part (12') moulded integrally with the first tubular connector (2'), the extremity of which has a pair of diametrically opposed frontal recesses (17'), as shown in FIG. 19. As will be seen, the central tubular part (12') constitutes a plunger member cooperating with the valve (7'), with the former being able to move axially with respect to the latter due to the relative rotation between the first tubular connector (2') and the second tubular connector (3').

The cam-follower ridges (11') engage smoothly in their respective cam tracks (13'), which have a substantially helical shape and are formed in diametrically opposite positions on the outside of an axially extended, central portion (14') of the intermediate tubular element (4'). The tubular plunger (12') of the first tubular connector (2') is engaged via this central tubular portion (14'), around which it can turn, subject to friction. The rotary coupling with friction between the tubular plunger (12') and the central portion (14') is performed in a way that avoids leaks between their respective facing walls, i.e. it provides a dynamic fluid seal. This effect is produced by the fact that the central tubular portion (14') has a terminal annular section (15') with walls of reduced thickness and an internal, radial, annular enlargement (16') arranged to form a contact seal against the external surface of the tubular plunger (12'). The annular enlargement (16') is illustrated in greater detail in FIG. 22, where it is in the state immediately preceding the axial insertion of the tubular plunger (12') during assembling of the first tubular connector (2') and the intermediate tubular element (4'). This assembling is performed by the irreversible snap coupling of the cam-follower ridges (11') onto the relative cam tracks (13').

The intermediate element (4') has an annular base (18') with an internal circumferential groove (19') that engages, via a substantially irreversible axial snap coupling, on an annular rib (20') formed on the outside of the body (21') of the second tubular element (3')

Inside the base (18'), the second tubular element (3') has a short, integral, axial appendage (23') that, together with the body (21') of the second tubular element (3'), delimits a chamber (24') for the valve (7'). This axial appendage (23') presents a conical surface (25') that defines an annular seat for the valve (7'). On the opposite side, the body (21') of the second tubular element (3') has a channelled surface (26'), coaxial to the outlet passageway (6') and formed by a halo of radial channels communicating with the outlet passageway (6') on one side and the respective axial channels (27') that laterally delimit the chamber (24') on the other. In addition, axial ridges (28'), the function of which will be explained in the following, are provided on the channelled surface (26') around the outlet passageway (6').

Reference numeral 29' indicates the shutter of the valve (7'). This shutter (29') is composed of cup-shaped elastic element, shown in the non-deformed state corresponding to the closed position of the valve (7') in FIG. 17, and in deformed state corresponding to the open position of the valve (7') in FIG. 18. This cup-shaped element (29') has a circular end wall (30') and a shell or side wall (31') with a cylindrical shape or, more suitably, a conical surface diverging towards the outlet passageway (6').

The end wall (30') can be of even thickness or, more suitably, be thicker towards its centre, as illustrated.

Similarly, the side wall (31') can be of even thickness or, more suitably, be thicker towards its free edge (32'), or rather the part furthest away from the end wall (30'), as illustrated.

The external circumferential edge (33') of the end wall (30') can be sharp, as in the case of the illustrated example, or rounded.

The cup-shaped element (29') is normally moulded as a single piece of soft elastic material, especially liquid silicone that is injection moulded using a central injection point.

The cup-shaped element (29') is coaxially housed inside the chamber (24') with its end wall (30') facing the inlet passageway (5') like a transversal diaphragm and resting against the end of the tubular plunger (12') with the recesses (17'). The side wall (31') of the cup-shaped element (29') faces the axial channels (27') with its free edge (32') resting against the channelled surface (26') of the second tubular element (3').

The external circumferential edge (33') of the end wall (30') of the cup-shaped element (29') cooperates with the annular valve seat (25') of the intermediate tubular element (4'). The arrangement is such that in the valve's closed position shown in FIGS. 13, 15 and 17, the cup-shaped element (29') is subjected to a predetermined axial preloading: in this way the peripheral edge (33') of the end wall (30') is kept elastically pressed against the annular valve seat (25') by the axial force exerted by the side wall (31'), as well as the radial force applied by the end wall (30') due to the conical shape of the valve seat (25'), forming a seal. This condition corresponds to the normally closed position of the valve (7'), in which flow from the upstream passageway (5') to the downstream passageway (6') is prevented in an effective and safe manner. This normally closed position is visually identifiable by the angular alignment between the radial projections (9') of the first tubular connector (2') and the pair of corresponding reference projections (34') on the intermediate tubular element (4').

When an overpressure exceeding a predetermined threshold, in the range 1–5 psi for example, develops in the upstream passageway (5'), the anti-siphon valve (7') passes automatically and promptly from the closed state to the open state, shown in FIG. 18, due to flexion of the end wall (30') of the cup-shaped element (29'), possibly combined with partial, axial, elastic yielding of its side wall (31'). This flexion causes the peripheral edge (33') of the end wall (30') of the cup-shaped element (29') to move away from the annular valve seat (25'), producing an annular opening between them (35'), as shown in FIG. 18. The upstream passageway (5') is thus in connection with the downstream passageway (6') via the annular opening (35'), the axial channels (27') facing the side wall (31') of the cup-shaped element (29') and the radial channels of the channelled wall (26') of the second tubular connector (3').

As already stated, the spontaneous opening of the valve (7') occurs promptly even if the diaphragm formed by the end wall (30') of the cup-shaped element (29') is subjected to a relatively high axial preloading for assuring maximum safety and reliability in closure. In fact, the force imparted against the end wall (30') by the pressure when it reaches the threshold value causes its elastic deformation into an essentially concave hemispheric shape, resulting in the peripheral edge (33') separating from the conical-surface valve seat (25') with a certain amount of amplification. Therefore, in practice a modest pressure beyond the threshold level is sufficient to cause the immediate and rapid opening of the valve (7'), thus reducing any risks of undesired adherence between the edge (33') and the valve seat (25'), even after the valve (7') has been closed for prolonged periods.

In the open state of the valve (7'), as the fluid flow increases, the end wall (30') of the cup-shaped element (29') becomes proportionally more deformed and, in consequence, the annular opening (35') proportionally increases in size.

The function of the axial ridges (28') on the channelled surface (26') is to prevent the end wall (30') from blocking the outlet passageway (6') when it becomes deformed.

In addition, in the open state of the valve (7'), the force imparted by the fluid against the external surface in the zone of the side wall (31') of the cup-shaped element (29') next to its end wall (30') contributes to keeping the valve open.

The anti-siphon valve (7') immediately returns to the closed position when the pressure balance between the upstream passageway (5') and the downstream passageway (6') is re-established, or in the case of overpressure in the downstream passageway (6'), due to the end wall (30') of the cup-shaped element (29') returning to the non-deflected configuration with the relative peripheral edge (33') resting against the annular valve seat (25'), as shown in FIG. 17.

To positively operate opening of the valve (7') it is sufficient to rotate the first tubular fitting (2') with respect to the intermediate tubular element (4'), or rather the first tubular fitting (2') with respect to the second tubular connector (3'), by manually turning the projections 9' and 34'. Due to this rotation, normally of approximately 900, and the interaction between the cam-follower ridges (11') and the cam tracks (13') from the state shown in FIGS. 13, 15 and 17 to that illustrated in FIGS. 14, 16 and 18, the reciprocal helical motion between the first tubular fitting (2') and the intermediate element (4'), or rather between the first tubular fitting (2') and the second tubular connector (3'), causes the tubular plunger (12') to axially advance from the retracted, inoperative position towards the advanced operative position. In doing so, it axially presses the end wall (30') of the cup-shaped element (29') in the direction of the outlet passageway (6'). The end wall (30') is thus deformed in the same way as that previously described with reference to spontaneous opening.

Figure 13:
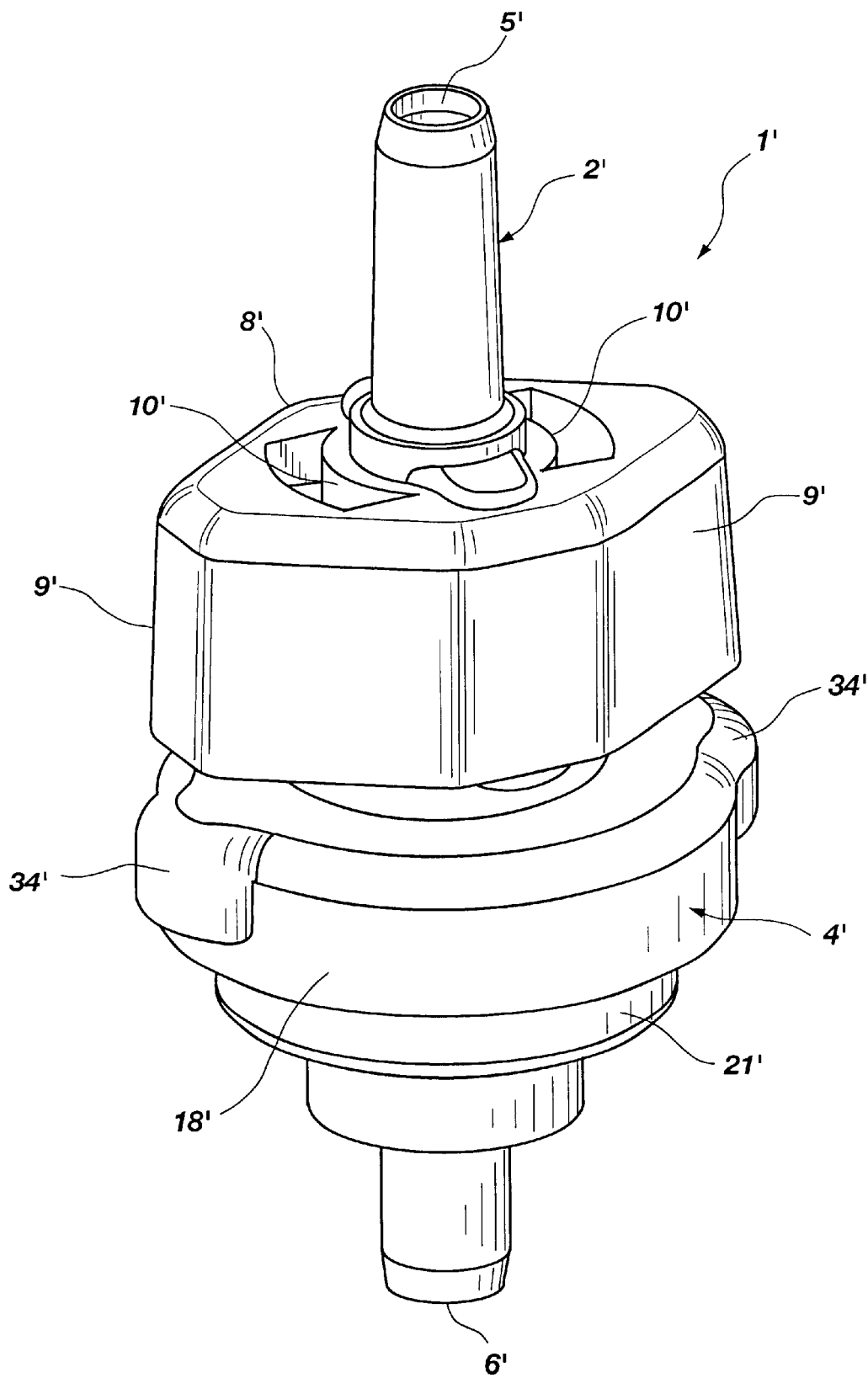
FIG. 13 is an enlarged perspective view of another variant of the check valve in conformity with the invention, with the valve shown in its normally closed position.
Figure 15:
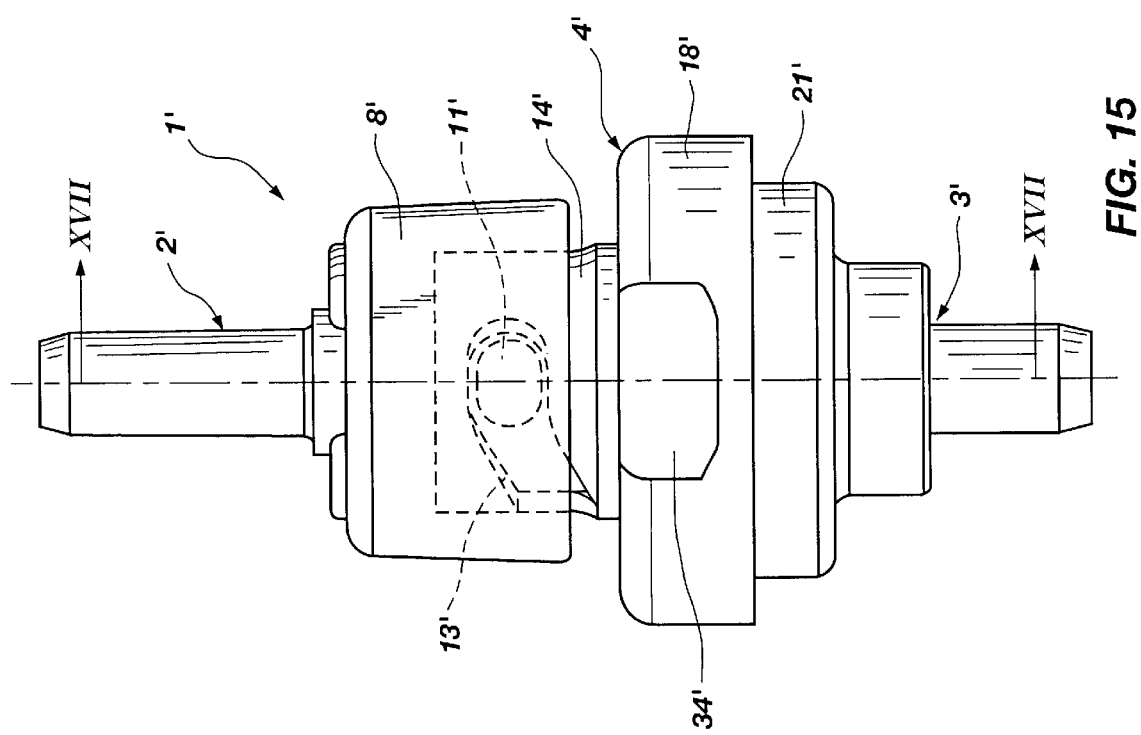
FIG. 15 is a side view of FIG. 13.

The open state thus obtained is maintained until the first tubular fitting (2') is rotated with respect to the intermediate tubular element (4'), back to the starting position in FIGS. 13, 15 and 17. In this case, the tubular plunger (12') is brought back to the retracted, inoperative position and the end wall (30') of the cup-shaped element (29') returns with its edge (33') in contact with the valve seat (25') to form a hermetic seal.

From the above description, it is evident that the system for moving the plunger (12') provides positive control for both opening and closing the valve (7') and that it allows the said tubular plunger (12') to be permanently held in either of the retracted or advanced positions.

It will also be appreciated that the manoeuvres for positively controlling opening and closing of the valve are practical and functional, and that assembling of the valve's component elements—effected via simple axial snap couplings—can be carried out in a relatively simple and economic manner and even using fully mechanised devices.

It should also be noted that the overall dimensions of the valve, or rather of the fitting (1') that incorporates it, are extremely small and in general are not greater than those of a similar connector with an anti-siphon valve that provides only spontaneous opening/closing.

Naturally, also in this case, the constructional details and the forms of realisation could be extensively changed with respect to that described and illustrated without departing from the scope of this invention, as defined in the appended claims.

Figure 14:
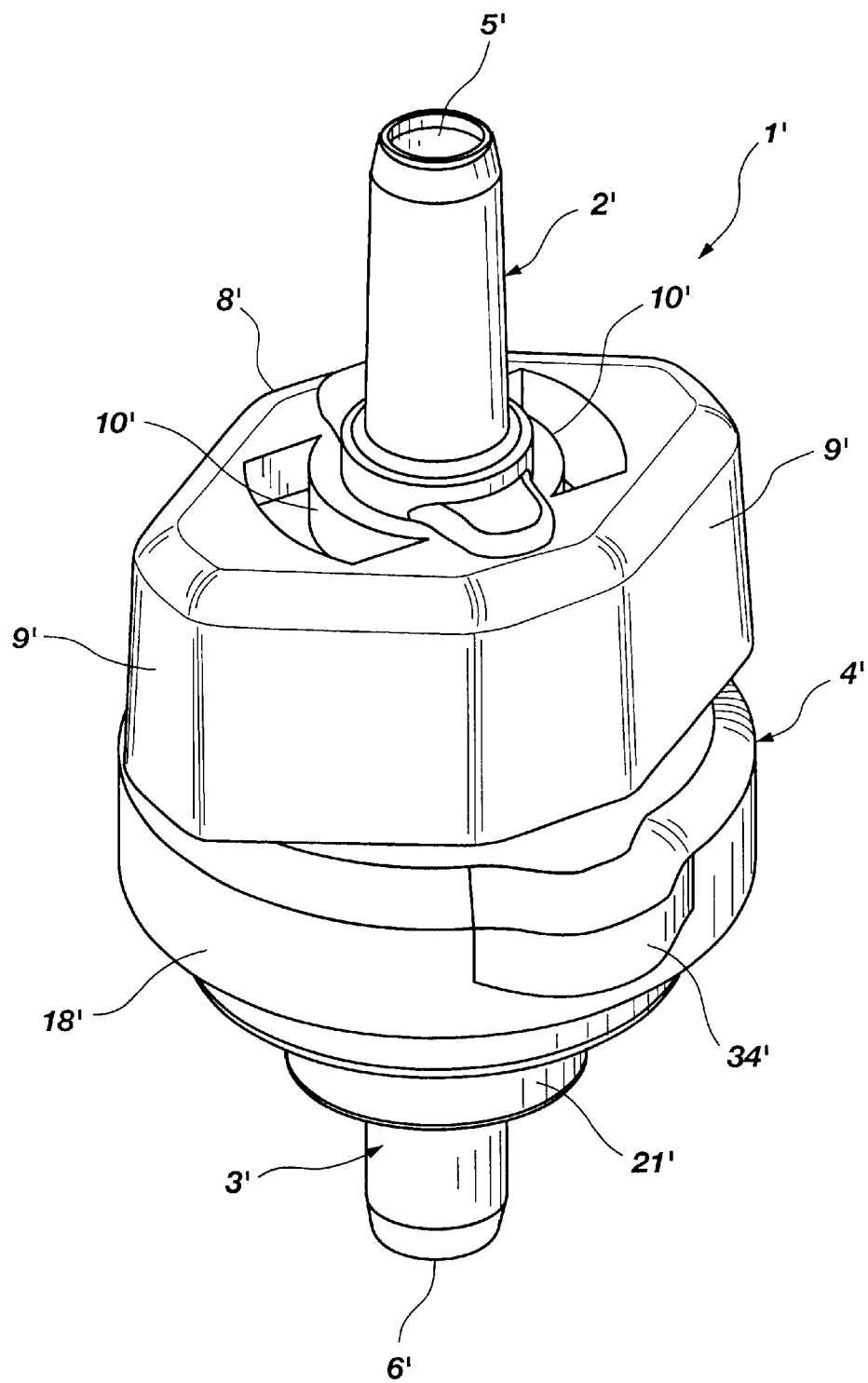
FIG. 14 is a similar view to that of FIG. 13, showing the valve in the open position.
Figure 16:
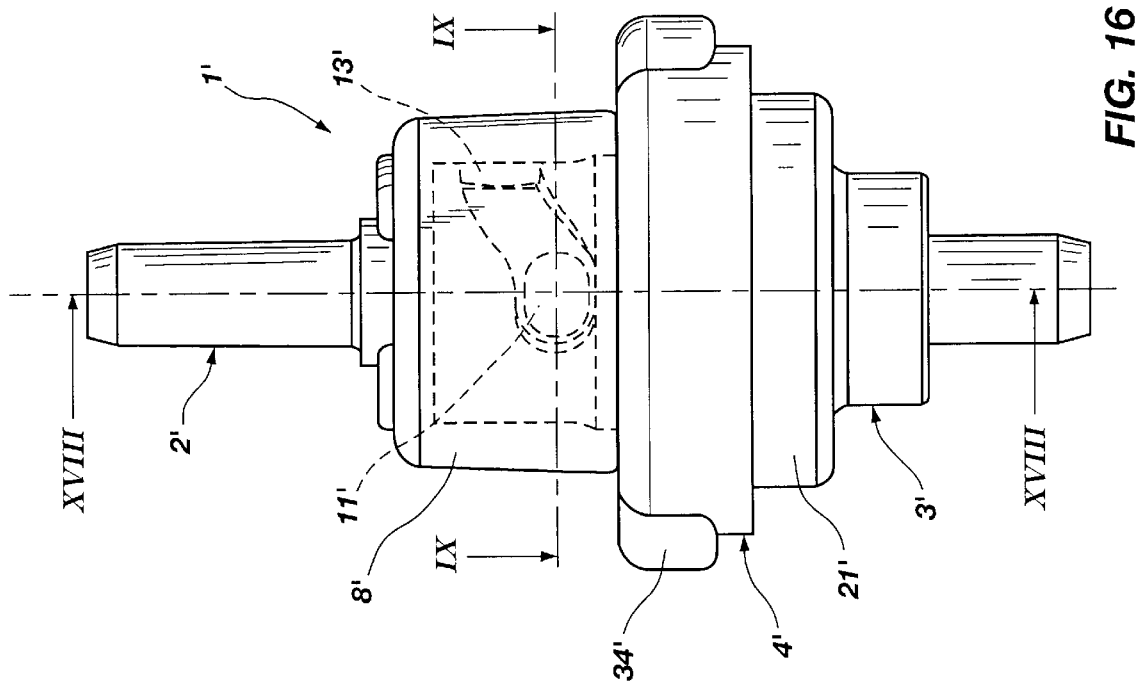
FIG. 16 is a side view of FIG. 14.

Thus, for example, the cam tracks (13') of the intermediate tubular element (4') could be arranged such that the reciprocal angular position between the manoeuvring protuberances (9') of the first tubular fitting (2') and the reference protuberances (34') of the intermediate tubular element (4') corresponds to that represented in FIGS. 13 and 15 when the valve (7') is in the closed position and that shown in FIGS. 14 and 16 corresponds instead to the open state of the valve (7').

In addition, although the valve has been described with express reference to anti-siphon applications, it could easily be adapted for use as a simple check valve with an opening control and a preset for spontaneous opening at significantly smaller fluid pressures, in the order of 0.01–0.02 bar for example. Calibration can be effected by simply working on the elastic characteristics of the cup-shaped element (29'), e.g. varying the thickness of its end wall (30'), using materials of different hardness, or modifying assembly pre-loading.

Finally, the cam system used for implementing controlled valve opening/closing could be substituted by any equivalent system, possibly with motorised actuation.

What is claimed is:

1. A check valve for medical infusion lines, said check valve comprising:
    a first and a second tubular element respectively defining an upstream passageway and a downstream passageway, wherein said upstream passageway is offset in parallel with respect to said downstream passageway;
    a diaphragm of elastically deformable material transversely positioned between said first and said second tubular elements and acting as a fluid seal in combination with an annular valve seat to keep the control valve normally closed, wherein a predetermined fluid pressure in said upstream passageway causes flexion of said diaphragm and the consequent opening of the valve;
    a plunger member offset in parallel with respect to said upstream passageway, said plunger member axially cooperating with said diaphragm and axially sliding between a retracted, inoperative position and an advanced, operative position to cause the controlled flexion of said diaphragm; and
    manually operable control structure for positively moving said plunger from said inoperative position to said operative position and hence cause controlled flexion of said diaphragm.

2. A valve according to claim 1, wherein said first and second tubular elements are set up for tube-tube, Luer-tube, tube-Luer or Luer-Luer connections on said medical line.

3. A valve according to claim 1, wherein an elastic structure for maintaining said plunger in the inoperative position is provided.

4. A valve according to claim 1, wherein said annular valve seat is defined by a wall with a conical surface coaxial to said downstream passageway and diverging towards the latter, and said diaphragm is constituted by an end wall of a cup-shaped element, said end wall having an external peripheral edge which is normally pressed against said annular valve seat to provide a seal under axial pressure exerted by the side wall of said cup-shaped element; flexion of said end wall of said cup-shaped element produced in use either by said predetermined fluid pressure, or by manoeuvring said control structure, causing radial contraction of said external peripheral edge and consequent separation thereof from said annular valve seat.

5. A valve according to claim 4, wherein said side wall of the cup-shaped element has a free edge in contact with a channeled surface of said second tubular element communicating with said downstream passageway.

6. A valve according to claim 5, wherein said channeled surface has a halo of radial channels, each extending into a respective axial channel facing the side wall of said cup-shaped element.

7. A valve according to claim 4, wherein said side wall of the cup-shaped element has a cylindrical surface.

8. A valve according to claim 4, wherein said side wall of the cup-shaped element has a conical surface diverging in the direction of said downstream passageway.

9. A valve according to claim 4, wherein said cup-shaped element has a variable thickness.

10. A valve according to claim 4, wherein said external peripheral edge of the end wall of said cup-shaped element has a sharp edge.

11. A valve according to claim 4, wherein said cup-shaped element is formed from a single piece of soft elastomeric material, namely liquid silicone that is injection molded using a central injection point.

12. A valve according to claim 4, wherein:
    said upstream passageway is staggered in parallel with respect to said downstream passageway,
    said valve seat and said diaphragm are arranged coaxially with respect to said downstream passageway,
    elastic means are provided for maintaining said plunger in said inoperative position, and
    cam control means can be manually operated to set Find maintain said plunger in said operative position, thereby causing the controlled flexion of said diaphragm.

13. A valve according to claim 12, wherein said elastic means are integrally formed with said plunger.

14. A valve according to claim 13, wherein said elastic means are composed of an elastically yielding annular wall interconnecting said plunger and said first hollow body and hermetically sealing said chamber.

15. A valve according to claim 14, wherein said elastically yielding annular wall is molded with annular ribbings.

16. A valve according to claim 12, wherein said first and second tubular elements are each formed as a single piece with a respective first and second hollow body, said hollow bodies being permanently coupled together to define a hermetically sealed chamber, containing said downstream, said annular valve seat and said plunger; said chamber being axially connected with said downstream passageway and laterally connected with said upstream passageway.

17. A valve according to claim 16, wherein said first and second hollow bodies are also equipped with integral axial appendages forming a fork support on the outside of said chamber and said means of cam control includes a transverse shaft that is supported in rotation by said support fork; said shaft carrying a radial cam acting on the plunger and equipped with actuating control means.

18. A valve according to claim 12, wherein the said cam control means is rotary.

19. A valve according to claim 12, wherein said elastic means are integrally formed with said first hollow body.

20. A valve according to claim 4, wherein said control means include a manually controlled cam mechanism for positively setting and maintaining said plunger in either the inoperative or the operative positions.

21. A valve according to claim 20, wherein said plunger is tubular.

22. A valve according to claim 4, wherein:
    said upstream passageway is staggered in parallel with respect to said downstream passageway,
    said valve seat and said diaphragm are arranged coaxially with respect to said downstream passageway,
    elastic structure are provided for maintaining said plunger in said inoperative position, and
    said control structure can be manually operated to set said plunger in said operative position, against the action of said elastic structure, thereby causing the controlled flexion of said diaphragm; the simple release of said control structure allowing immediate return of the valve to said closed position under the action of said elastic structure.

23. A valve according to claim 22, wherein said control structure is configured to slide.

24. A valve according to claim 23, wherein said elastic structure comprises an elastically yielding annular wall that interconnects said plunger with said first hollow body and hermetically seals said chamber.

25. A valve according to claim 24, wherein said elastically yielding annular wall has a, substantially bell-shaped form.

26. A valve according to claim 24, wherein the said elastically yielding annular wall is formed with annular ribbings.

27. A valve according to claim 22, wherein said elastic structure is integrally formed with said plunger.

28. A valve according to claim 22, characterized in that the said plunger (9) is formed with axial recesses.

29. A valve according to claim 22, wherein said annular valve seat is formed in an annular member through which said plunger axially slides.

30. A valve according to claim 22, wherein said first and second tubular elements are each formed as a single piece with a respective first and second hollow body, said hollow bodies being permanently coupled together to define a hermetically sealed chamber containing said diaphragm, said annular valve seat and said plunger; said chamber being axially connected with said downstream passageway and laterally connected with said upstream passageway.

31. A valve according to claim 30, wherein said elastic structure is integrally formed with said first hollow body.

32. A check valve (1) for medical infusion lines and the like, including a first and a second tubular element (5, 13) that respectively define an axial upstream passageway (6) and an axial downstream passageway (14), a diaphragm (17) of elastically deformable material transversely positioned between said first and a second tubular elements (5, 13) and acting as a fluid seal in combination with an annular valve seat (25) to keep said valve normally closed, wherein a predetermined fluid pressure in said upstream passageway (6) causes flexion of said diaphragm (18) and the consequent opening of the valve, wherein:
    said upstream passageway (6) is offset in parallel with respect to said downstream passageway (14),
    said valve seat (25) and said diaphragm (17) are arranged coaxially with respect to said downstream passageway (14), said diaphragm (17) coaxially rests on a plunger member (9) that can slide between a retracted, inoperative position and an advanced, operative positions said plunger member (9) being offset in parallel with respect of said upstream passageway;

elastic structure (8) is provided for normally maintaining said plunger member (9) in said inoperative position, and manually operated control structure (10) is provided to set said plunger member (9) in said operative position, against the action of said elastic structure (8), thereby causing the controlled flexion of said diaphragm (17); the simple release of said control structure (10) allows the immediate return of the valve (1) to said closed position under the action of said elastic structure (8).

33. A check valve (1) for medical infusion lines and the like, including a first and a second tubular element (5, 13) that respectively define an axial upstream passageway (6) and an axial downstream passageway (14), a diaphragm (17) of elastically deformable material transversely positioned between said first and a second tubular element (5, 13) and acting as a fluid seal in combination with an annular valve seat (25) to keep said valve normally closed, wherein a predetermined fluid pressure in said upstream passageway (6) causes flexion of said diaphragm (18) and the consequent opening of the valve, wherein:

said upstream passageway (6) is offset in parallel with respect to said downstream passageway (14), said valve seat (25) and said diaphragm (17) are arranged coaxially with respect to said downstream passageway (14), the diaphragm (17) coaxially rests on a plunger member (9) that can slide between a retracted, inoperative position and an advanced, operative position, said plunger member (9) being offset in parallel with respect of said upstream passageway;

elastic structure (8) is provided for normally maintaining said plunger (9) in said inoperative position, and a manually operated cam control mechanism (29, 32) is provided to set said plunger (9) in said operative position, thereby causing the controlled flexion of said diaphragm (17).

34. A check valve (7')for medical infusion lines and the like, including a first and a second tubular element (2', 3') mutually coaxial to each other and respectively defining an upstream passageway (5') and a downstream passageway (6'), said upstream passageway (5') being offset in parallel with respect to said downstream passageway (6'), a diaphragm (30') of elastically deformable material transversely positioned between said first and a second tubular elements (2', 3') and acting as a fluid seal in combination with an annular valve seat (25 ) to keep said valve normally closed wherein a predetermined fluid pressure in said upstream passageway (5') causes flexion of said diaphragm (30') and the consequent opening of said valve (7'), further comprising a tubular plunger member (12') coaxially cooperating with said diaphragm (30'), said tubular plunger member (12') being axially slidable between a retracted inoperative position and an advanced operative position to cause controlled flexion of said diaphragm (30'), said plunger member (12') being offset in parallel with respect of said upstream passageway (5'); and also comprising a cam control structure (11', 13') manually operable to positively set and maintain said plunger (12') in either said inoperative position or said operative position.

* * * * *